United States Patent
Baumann et al.

(10) Patent No.: US 6,362,347 B1
(45) Date of Patent: Mar. 26, 2002

(54) METHOD FOR PURIFYING PHTHALIDES

(75) Inventors: Dieter Baumann, Walldorf; Hermann Pütter, Neustadt; Heinz Hannebaum, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/508,619

(22) PCT Filed: Sep. 18, 1998

(86) PCT No.: PCT/EP98/05983

§ 371 Date: Mar. 14, 2000

§ 102(e) Date: Mar. 14, 2000

(87) PCT Pub. No.: WO99/15515

PCT Pub. Date: Apr. 1, 1999

(30) Foreign Application Priority Data

Sep. 19, 1997 (DE) .......................................... 197 41 423
Oct. 15, 1997 (DE) .......................................... 197 45 579

(51) Int. Cl.⁷ .............................................. C07D 307/88
(52) U.S. Cl. ....................................................... 549/307
(58) Field of Search ......................................... 549/307

(56) References Cited

FOREIGN PATENT DOCUMENTS

| DE | 21 44 419 | 8/1973 |
|---|---|---|
| DE | 25 10 920 | 9/1976 |
| WO | WO 97/43464 | 10/1997 |

*Primary Examiner*—T. A. Solola
(74) *Attorney, Agent, or Firm*—Keil & Weinkauf

(57) ABSTRACT

Phthalides in as-obtained phthalide synthesis reaction mixtures are recovered in pure form by (a) distilling compounds having a boiling point below the boiling point of the phthalide from the reaction mixture, provided such compounds are present in the reaction mixture, to obtain a crude phthalide as bottom product, (b) crystallizing the phthalide from a melt of the crude phthalide.

14 Claims, No Drawings

METHOD FOR PURIFYING PHTHALIDES

The present invention relates to a process for recovering phthalides from as-obtained phthalide synthesis reaction mixtures.

Phthalides, i.e., substituted lactones of 2-(hydroxymethyl)benzoic acid, and phthalide itself (isobenzofuran-1(3H)-one) are required especially as intermediates for the synthesis of crop protection agents or drugs.

Various processes for preparing phthalides are known. Phthalides are predominantly prepared by means of electrochemical processes, by homogeneously or heterogeneously catalyzed hydrogenation.

DE-A 21 44 419 describes a process for the electrochemical preparation of phthalide. An aqueous solution of ammonium phthalamate is cathodic ally reduced at electrolysis temperatures of up to 65° C. over metals having a hydrogen overpotential greater than that of copper. High purity lead in particular is used as cathode material. To work up, any excess ammonia and solvent and some of the water are distilled off. A solution of the primary reaction product, the ammonium salt of o-aminomethylbenzoic acid, is left behind and is treated with a strong acid to precipitate phthalide. The phthalide is isolated by filtration. Product still in solution can be extracted with benzene. The product obtained can be further purified by recrystallization from hot water.

DE-A 25 10 920 describes a process for electrochemical preparation of phthalide. An ammoniacal aqueous solution of phthalic anhydride or acid is cathodically reduced at up to 100° C. over metals having a hydrogen overpotential greater than that of copper. The reaction mixture is worked up by distilling any excess ammonia and/or water out of the electrolysis mixture to separate off the phthalide and acidifying the residue at from 35 to 100° C.

Prior DE-A 196 18 854, unpublished at the priority date of the present invention, describes a process for preparing phthalides by cathodic reduction of phthalic acid derivatives. Reduction is carried out in an organic solvent comprising less than 50% by weight of water in an undivided electrolysis cell. It is stated that the workup can be effected by distillation, precipitation or recrystallization. In addition, the phthalides can be dissolved in ammoniacal aqueous solutions, then the aqueous phase separated off and the phthalide reprecipitated by acidification of the aqueous phase. The exemplified workup involves distillative removal of the solvent mixture and vacuum distillation of the phthalide.

The distillation has to be carried out at a high temperature level in the region of the boiling point of the phthalides, so that the product is subjected to considerable thermal stress for a prolonged period. In addition, distillation is not in all cases suitable for obtaining a pure phthalide. Specifically in the case of the electrochemical preparation of phthalides starting from methyl phthalates, unconverted methyl phthalates and phthalide form an azeotrope which cannot be separated by distillation. If the proportion of methyl phthalate remaining in the product is to be minimized by the way the reaction is conducted, the phthalide yield decreases and other, secondary products can appear.

Recrystallizing the phthalides involves dissolving them in a solvent and cooling the solution to crystallize them out again. It is thus necessary to provide a solvent and to separate it again from the pure phthalide at some inconvenience. Handling the solvent in a closed-loop system requires complex processing technology. After the crystallizate has been separated from the mother liquor, the mother liquor has to be concentrated in order that it may be further processed. The product obtained may include residual solvent, which has to be removed by drying.

It is an object of the present invention to provide a process for recovering phthalides from as-obtained phthalide synthesis reaction mixtures without the disadvantages of existing workups. More particularly, the process shall not require the use of solvents or of other assistants, shall keep the thermal stress on the phthalides to a minimum and shall be economical to carry out in energy terms.

We have found that this object is achieved according to the invention by a process for recovering phthalide from an as-obtained phthalide synthesis reaction mixture by (a) distilling compounds having a boiling point below the boiling point of the phthalide from the reaction mixture, provided such compounds are present in the reaction mixture, to obtain a crude phthalide as bottom product, (b) crystallizing the phthalide from a melt of the crude phthalide.

The phthalide is crystallized from a melt of the crude phthalide, i.e., without use of other solvents or other assistants, as required, for example, for a recrystallization.

The solvent-free crude phthalide is in turn obtained from the reaction mixture by distillative removal of compounds having a lower boiling point than the desired phthalides. If such compounds are present in the reaction mixtures, they are thus removed by distillation prior to the crystallization. The bottom product of the distillation is a crude phthalide, and the thermal stress involved in removing the low boiling compounds is considerably less than the thermal stress that would be involved in an additional, subsequent distillation of the phthalide. The crude phthalide used for the crystallization is thus substantially or, preferably, completely free from solvents or lower boiling compounds.

In one embodiment of the invention, the crystallizing is effected on a cooled surface on which the crystals grow.

So the liquid crude phthalide is brought into contact with a cooling surface, and phthalide crystals are formed thereon. On completion of the crystallization phase, the remaining liquid (mother liquor) is removed. The purity of the phthalide crystals remaining on the cooling surface can be increased by partially melting off (sweating) comparatively impurer portions of the crystals. In addition, the purity of the crystals on the cooling surface can be increased by washing, for example with the crude phthalide feed or with liquid phthalide of higher purity. Finally, the purified crystals are liquefied by heating, and the resulting melt of the pure phthalide is removed from the cooling surface.

The cooling surface where the crystallization is carried out is not subject to any restriction; it may have any desired suitable shape. The temperature of the melt during the crystallization is preferably within the range from −10 to 75° C., particularly preferably within the range from 20 to 70° C. The solids content in the crystallizer is customarily within the range from 10 to 90 g, preferably within the range from 30 to 80 g, per 100 g of crude phthalide feed.

The crystallization can be carried out continuously or batchwise, in one stage or in a plurality of stages.

The crystallization on the cooled surface can be carried out as a static crystallization or as a dynamic layer crystallization. In the first case, the crude phthalide melt used is stationary. Such a static crystallization process is available for example from BEFS/Prokem (France) or from Sulzer Chemtech (Switzerland). In a dynamic layer crystallization, the melt of the crude phthalide is subjected to forced convection. Such a process is available for example from Sulzer Chemtech (Switzerland). In both process variants, the cooled surfaces are disposed inside the crystallization apparatus, so that the crystals which form are immobilized inside the apparatus. Preference is given to the use of a static crystallization, where the melt of the crude phthalide is stationary and only natural convection occurs.

The advantage of this process is that the product is subjected to only a very low thermal stress and that the temperature level required is low, keeping the energy requirement relatively low. The separation of crystals from the mother liquor can be effected without additional equipment requirements.

The crystallization on a cooled surface is preferably effected in multiple stages as a fractional crystallization. Fractional crystallization can also be employed in the case of the other suitable crystallization processes, for example suspension crystallization.

Fractional crystallization makes it possible to raise the purity of the phthalides if one purification stage is not enough to achieve the desired end-purity. Repeated crystallization of the respectively produced pure fractions, which are then liquefied, can be used to achieve the desired end-purity.

In a fractional crystallization, all stages producing crystals of a purity higher than that of the crude phthalide feed are customarily referred to as purification stages, while all other stages are known as stripping stages. Multi-stage processes are advantageously operated according to the countercurrent principle, whereby, in each stage, the crystallizate is separated from the mother liquor after the crystallization, and this crystallizate is fed into whichever is the stage having the next highest degree of purity, while the crystallization residue is fed into the particular stage having the next lowest degree of purity.

The fractional crystallization is preferably carried out with from 2 to 10 stages, particularly preferably with from 2 to 4 stages, especially with 3 stages.

In a suspension crystallization, the melt of the crude phthalide is crystallized by heat removal. The crystals which form are in suspension in the remaining liquid phase (mother liquor). On attainment of a desired crystal content, customarily within the range from 10 to 40% by weight, the crystals are separated from the mother liquor. After separation, the crystals can be liquefied and crystallized in a further stage.

Heat removal can be effected by cooling in a heat transferor, preferably a tube bundle heat transferor, through which the suspension passes, preferably on the tube side. If encrustation of the cooling surface is likely, a plurality of heat transferors, preferably 3 heat transferors, can be connected in parallel. One of the heat transferors is always taken out of service, and the adhering phthalide crystals can be melted off by heating. This permits continuous operation. For example, the thermal conductivity of the heat transferor can be measured in operation. When the thermal conductivity has become excessively low due to crystal layer formation, operation is switched to a second heat transferor and so on. As well as melting off the adhering crystals, they can also be removed by purging the heat transferor with a feed solution of the phthalide. This also enables the feed to be precooled at the same time.

The residence time required for crystal growth is made available in a crystallizer, preferably a forced circulation crystallizer, whose suspension circuit accommodates the heat transferors.

In addition, heat removal from the suspension can be obtained by means of a heat transferor having scraped cooling surfaces. Heat is removed via scrape coolers connected to a stirred tank or to a vessel without a stirrer. Circulation of the crystal suspension is insured in this case by means of a pump. Alternatively, it is often possible to remove the heat via the walls of a stirred tank having a close-clearance stirrer. A further possibility is to combine heat removal and residence time control in one piece of equipment. This is the case for example with a cooling disk crystallizer as available for example from Goudsche Machinefabrik B.V. (Netherlands). The heat is removed via cooled plates which are wiped on both sides to avoid encrustations. The cooling plates are disposed in a cuboid shaped vessel in such a way that they divide it into equidimensional segments, each of which is bounded by a cooling surface on both sides. The suspension moves from segment to segment and has a very narrow residence time spectrum. The cooling medium flowing within the cooling plates flows in the direction opposite to the flow direction of the suspension. As a result, the suspension passing through the equipment undergoes a virtually continuous temperature lowering and correspondingly has an increasing crystal content.

The mother liquor and the crystallized phthalide can be suitably separated using any known solid-liquid separation process. For example, the crystals can be separated from the suspension via a centrifuge, especially a pusher centrifuge, or a filter, particularly preferably a belt filter or a turntable filter. Filtration or centrifugation can be preceded by a prethickening of the suspension, for example by means of hydrocyclones. As well as single- or multi-stage pusher centrifuges, it is also possible to use screw centrifuges or screw discharge centrifuges (decanters). Filtration can be effected batchwise or continuously, under superatmospheric pressure or at reduced pressure. If suction filters are used, they can be equipped with a stirrer.

Solid-liquid separation may be accompanied and/or followed by further process steps for increasing the purity of the crystals or of the crystal cake. The crystals obtained in stage (b) can be further purified for example by washing and/or sweating. In washing, the quantity of wash liquor is preferably within the range from 10 to 500 g of wash liquor/100 g of crystallizate, particularly preferably within the range from 30 to 200 g of wash liquor/100 g of crystallizate. Suitable wash liquors are for example the liquid pure product which is obtained by melting the crystals obtained, or the liquid crude phthalide. The washing medium should have a higher purity than the mother liquor from which the crystallizate was removed. Washing or sweating may in certain circumstances save a further purification or crystallization step.

Washing can be effected in a customary washing apparatus. It is advantageous to use wash columns in which the removal of the mother liquor and the washing take place in one and the same apparatus, centrifuges, which can be operated in one or more stages, or suction filters or belt filters. The washing can be carried out on centrifuges or belt filters in one or more stages. The wash liquor can be passed in countercurrent to the crystal cake.

Sweating describes a local melting-off of impure regions of the crystals. The sweat quantity is advantageously within the range from 5 to 35 g of molten-off crystallizate/100 g of crystallizate prior to sweating. It is particularly preferable to carry out the sweating on belt filters. A combined wash and sweat in one apparatus can also be suitable.

A further way to increase the purity is to slurry up the removed crystallizate and to subject the slurry to another separation. The slurry can be formed in pure product or in the melt of the crude phthalide.

The purity of the phthalide obtained is preferably within the range from 97 to 99.9% by weight, especially within the range from 98.5 to 99.5% by weight.

The step (b) crystallization of the phthalide from the melt of the crude phthalide is particularly preferably effected by three-stage static melt crystallization.

The reaction mixture from which the phthalides are isolated can originate in any desired manufacturing process for the synthesis of pthalides. For example, it can be produced in an electrolytic reduction as described for example in DE-A 21 44 419 and DE-A 25 10 920 or DE-A 196 18 854. The reaction mixture may here comprise solvents, conducting salts, anodic depolarizers, mediators or mixtures thereof.

In the electrolytic reduction process, especially phthalic acid or phthalic acid derivatives in which the carboxyl groups may be replaced by units derived from carboxyl groups in a condensation reaction, and one or more of the hydrogens of the o-phenylene unit of phthalic acid may be substituted by inert radicals, are dissolved in an electrolyte and reduced at a cathode in an undivided electrolysis cell.

The starting compounds used for preparing the phthalides are in particular those of the general formula (I)

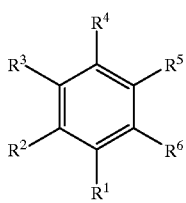

(I)

where the substituents have the following meanings:

$R^1, R^2, R^3$ and $R^4$: are each, independently of one another, hydrogen, $C_1$–$C_4$-alkyl or halogen, $R^5, R^6$:
(a) are each, independently of each other, —COOH or COOX, where X is $C_1$–$C_4$-alkyl,
(b) one of the substituents $R^5$ or $R^6$ is —COONY$_2$ and the other substituent is CONH$_2$, where Y is $C_1$–$C_4$-alkyl or hydrogen,
(c) $R^5$ and $R^6$ are together —CO—O—CO—.

Particular preference is given to those derivatives of phthalic acid where $R^1$, $R^2$, $R^3$ and $R^4$ are each hydrogen, and among these especially to the di-($C_1$–$C_3$-alkyl) phthalates, in particular to dimethyl phthalate.

The electrochemical conversion of these starting materials can be effected for example by the method described in DE-A 196 18 854.

The electrolyte is customarily a 2–40% strength by weight solution of phthalic acid or of a phthalic acid derivative in an organic solvent or a mixture of an organic solvent and water, the mixture generally comprising less than 50% by weight, preferably less than 25% by weight, particularly preferably less than 5% by weight, of water.

Useful organic solvents are in particular aliphatic $C_1$–$C_4$-alcohols, especially methanol or ethanol, or mixtures of such alcohols with a carboxamide such as dimethylformamide or tert-butylformamide.

Examples of conducting salts present in the electrolytes are quaternary ammonium salts, such as tetra($C_1$–$C_4$-alkyl) ammonium halides or tetrafluoroborates and preferably methyltributylammonium or methyltriethylammonium methosulfate, customarily in amounts of from 0.4 to 10% by weight, based on the electrolyte.

For the anodic coproduction process it is advisable to use as anodic depolarizer customary organic compounds whose suitability for electrochemical oxidation is common knowledge among those skilled in the art. Some anodic coproduction processes are preferably carried out in the presence of a mediator. Suitable anodic coproduction processes are described for example in D. Kyriakou, Modern Electroorganic Chemistry, Springer, Berlin 1994, chapter 4.2.

Suitable anodic coproduction processes are especially the oxidations of C—O or C—N single or double bonds, for example the oxidation of carboxylic acids, or the oxidative C—C coupling especially of napthalenes or activated CH groups and the oxidation of methyl groups attached to an aromatic nucleus to give aldehydes.

It is particularly advantageous to use methylbenzene or ring-substituted derivatives of methylbenzene, where from 1 to 3 hydrogen atoms of the phenyl radical can be replaced by $C_1$–$C_6$-alkyl radicals or $C_1$–$C_4$-alkoxy radicals. Examples of such anodic depolarizers are p-xylene and p-tert-butyltoluene.

When preparing aldehydes as coproducts, it is advisable to use the alcohols mentioned as solvents, since the aldehydes are acetalized and protected against further oxidation.

Suitable mediators are in particular halogen compounds, especially bromides or iodides.

The other process parameters such as temperature and current density are not crucial, as long as they are kept within the customary framework for electrochemical conversions of organic compounds. They are more particularly specified in DE-A 25 10 920 for example.

When the reaction has proceeded to the stage where the molar ratio (M) of the portion of phthalide to the sum of the proportion of phthalide and phthalic acid or phthalic acid derivatives in the electrolyte is within the range from 0.8:1 to 0.99:1, preferably within the range from 0.88:1 to 0.95:1, the electrolyte is discharged from the electrolytic cell.

The reaction can be carried out both batchwise and continuously.

If the reaction process is carried out continuously, it is advantageous to adjust the continuous discharge of the electrolyte and the continuous supplementation of the inert constituents of the electrolyte, as of the solvents and conducting salts and of the starting materials for the electrochemical reaction, to each other and to the reaction rate in such a way that the concentration of all constituents of the electrolyte remains essentially constant. This applies in particular to the molar ratio (M) which varies within the range defined.

In general, the discharged electrolyte, i.e., the reaction mixture, is worked up distillatively prior to crystallization, as described above.

The mother liquor formed in the purification process of the invention and any wash liquor obtained can be recycled into the electrolysis cell without further workup, since they consist essentially of a mixture of phthalide and the corresponding starting compound.

The reaction mixture used for purification can be obtained from the homogeneously or heterogeneously catalyzed hydrogenation of phthalic acid derivatives.

The composition of the reaction mixture, the underlying reaction and the catalysts used are described for example in EP-A-0 542 037, EP-A-0 089 417, EP-A-0 420 062 and DE-A-32 45 544.

We claim:

1. The process of recovery for phthalide from an as-obtainable phthalide synthesis reaction mixture by
(a) distilling compounds having a boiling point below the boiling point of said phthalide from said reaction mixture, provided such compounds are present in said reaction mixtures, to obtain a crude phthalide as bottom product, (b) crystallizing said phthalide from a melt of said crude phthalide without use of other solvents or other assistants.

2. The process of claim 1, wherein said crystallizing is effected on a cooled surface on which the crystals grow.

3. The process of claim 1, wherein said crystallizing is effected as a suspension crystallization.

4. The process of claim 1, wherein said crystallizing is effected in multiple stages as a fractional crystallization.

5. The process of claim 1, wherein the crystals obtained in step (b) are further purified by washing.

6. The process of claim 1, wherein the crystals obtained in step (b) are further purified by sweating by local melting-off of impure regions of the crystals.

7. The process of claim 1, wherein the crystals obtained in step (b) are further purified by washing and sweating.

8. The process of claim 1, wherein said reaction mixture is obtained from an electrolytic reduction.

9. The process of claim 8, wherein said reaction mixture comprises solvents, conducting salts, anodic depolarizers, mediators or mixtures thereof.

10. The process of claim 1, wherein said reaction mixture is obtained from a homogeneously catalyzed hydrogenation of phthalic acid derivatives in the presence of a catalyst comprising ruthenium and an organic phosphine.

11. The process of claim 1, wherein in said reaction mixture is obtained from a heterogeneously catalyzed hydrogenation of phthalic acid derivative in the presence of a hydrogenation catalyst, which is essentially free from Lewis acids or a nickel catalyst of low nickel content.

12. A process for recovering phthalide from an as-obtained phthalide synthesis reaction mixture by (a) distilling compounds having a boiling point below the boiling point of said phthalide from said reaction mixture, provided such compounds are present in said reaction mixtures, to obtain a crude phthalide as bottom product, (b) crystallizing said phthalide from a melt of said crude phthalide without use of other solvents or other assistants wherein said crystallizing is effected on a cooled surface on which the crystals grow.

13. The process of recovery for phthalide from an as-obtainable phthalide synthesis reaction mixture by (a) distilling compounds having a boiling point below the boiling point of said phthalide from said reaction mixture, provided such compounds are present in said reaction mixtures, to obtain a crude phthalide as bottom product, (b) crystallizing said phthalide from a melt of said crude phthalide without use of other solvents or other assistants, wherein said crystallizing is effected as a suspension crystallization, wherein the heat removed is effected by cooling in a heat transferor.

14. The process of claim 6, wherein the sweating is carried out on belt filters.

* * * * *